(12) United States Patent
DeHart

(10) Patent No.: US 6,798,215 B2
(45) Date of Patent: Sep. 28, 2004

(54) SYSTEM AND METHOD FOR MEASURING MOISTURE CONTENT IN A CONDUCTIVE ENVIRONMENT

(75) Inventor: Scott Alan DeHart, Eagle, ID (US)

(73) Assignee: Baseline, LLC, Boise, ID (US)

( * ) Notice: Subject to any disclaimer, the term of this patent is extended or adjusted under 35 U.S.C. 154(b) by 26 days.

(21) Appl. No.: 10/256,484

(22) Filed: Sep. 26, 2002

(65) Prior Publication Data

US 2003/0076120 A1 Apr. 24, 2003

Related U.S. Application Data

(60) Provisional application No. 60/326,057, filed on Sep. 28, 2001.

(51) Int. Cl.[7] ............................ G01R 27/04; G01R 27/08
(52) U.S. Cl. ........................................ 324/640; 324/694
(58) Field of Search ................................ 324/694, 676, 324/639, 640, 637, 663, 664, 643, 76.35, 76.54, 633; 239/63, 67; 73/304 C

(56) References Cited

U.S. PATENT DOCUMENTS

| | | | | |
|---|---|---|---|---|
| 4,470,008 A | * | 9/1984 | Kato | 327/4 |
| 5,315,258 A | * | 5/1994 | Jakkula et al. | 324/640 |
| 5,341,673 A | * | 8/1994 | Burns et al. | 73/73 |
| 6,657,443 B2 | * | 12/2003 | Anderson | 324/664 |

* cited by examiner

Primary Examiner—Anjan K. Deb
(74) Attorney, Agent, or Firm—Belnap & Curtis, PLLC; Robert A. Huntsman

(57) ABSTRACT

Accurate and stable measurement of the dielectric constant of the substance or a mixture of substances by the use of measuring the delay through a transmission line imbedded in the substance as a delay means with compensation for signal degradation brought about by conductivity of the substance. The substance for which the dielectric constant is to be measured is introduced between or about the elements of the transmission line so as to vary the propagation or delay of the signals through the transmission line.

14 Claims, 2 Drawing Sheets

SYSTEM AND METHOD FOR MEASURING MOISTURE CONTENT IN A CONDUCTIVE ENVIRONMENT

This application claims priority based on provision application 60 326 057 (sensor) filed on Sep. 28, 2001.

FIELD OF THE INVENTION

This invention relates to the use of delay through a delay line for measuring the dielectric properties of materials surrounding the delay line, in particular for the measurement of the dielectric constant where changes of conductivity affect the delay time.

DESCRIPTION OF THE RELEVANT ART

The concept of measuring dielectric constant through the use of a delay line is taught by Friedman in U.S. Pat. No. 3,965,416. Friedman further teaches the delay line can be integrally coupled as a portion of an oscillator and produce a frequency that is a function of the dielectric constant. The measured frequency can then be used to determine the dielectric constant.

Woodhead, et al., in U.S. Pat. No. 5,148,125, teaches that the delay line can specifically be used as the feedback element in a simple oscillator structure and produce an output frequency that is proportional to the dielectric constant. Woodhead specifically applies this technique to the measurement of soil moisture. While the teachings of Woodhead provide the teaching necessary to construct a simple sensor, the sensor tended taught by Woodhead tends to be heavily influenced by the electrical conductivity of the medium. The conductivity of soil is dependent upon soil salts, temperature and composition. The losses in the medium tend to slow the rise time and therefore make the delay longer than just the propagation through the delay line would indicate. In a sensor derived from Woodhead's teachings, the sample would appear to be moister that it actually was. Woodhead's teachings acknowledge this in the following statement, "the influence of losses due to solid conductivity may be reduced by insulating the line, although the volume of soil sampled and therefore the influence of soil moisture via capacitance is also reduced." The need to compensate for temperature effects on the dielectric constant is well known, but Woodhead's teachings fail to instruct in how to compensate for these changes.

Hocker U.S. Pat. No. 5,430,384) teaches the use of soil resistivity measurement to determine soil moisture content. However, fertilization adds ions that change the conductivity and hence change the moisture measurement reading.

Feuer, in U.S. Pat. No. 5,445,178, also teaches that "the use of an LC oscillator can minimize the adverse effects of the conductivity variances in the medium being monitored, because the resistance of the medium, (and, thus, the medium's conductivity) has minimal or now effect on the resonant frequency of an LC oscillator circuit." While this method is effective in many cases, the frequencies are generally very high. This method is thus limited by the capacitor's size and therefore, the propagation time across the capacitive plate or rod further limit the effective measuring area. Also, as the length of the capacitor grows, the resistance decreases until it can again affect the accuracy of the instrument.

SUMMARY OF THE INVENTION

It is the object of the present invention to provide a dielectric monitor which allows the measurement of moisture content or content of any other materials with a high dielectric constant averaged over an extended volume of material where the sensor has the ability to compensate for some level of variable conductivity.

Accordingly, the invention provides a method where the rise time of the pulse arriving from the transmission line is used to compute a correction for the delay time induced by the pulse degradation caused by loss of signal strength due to the conductivity of the sample. It also provides a method to compute a correction factor for temperature effects. We also demonstrate three independent sensing apparatus that each utilizes the correction method above.

DETAILED DESCRIPTION OF THE PREFERRED EMBODIMENT

Figure 1:
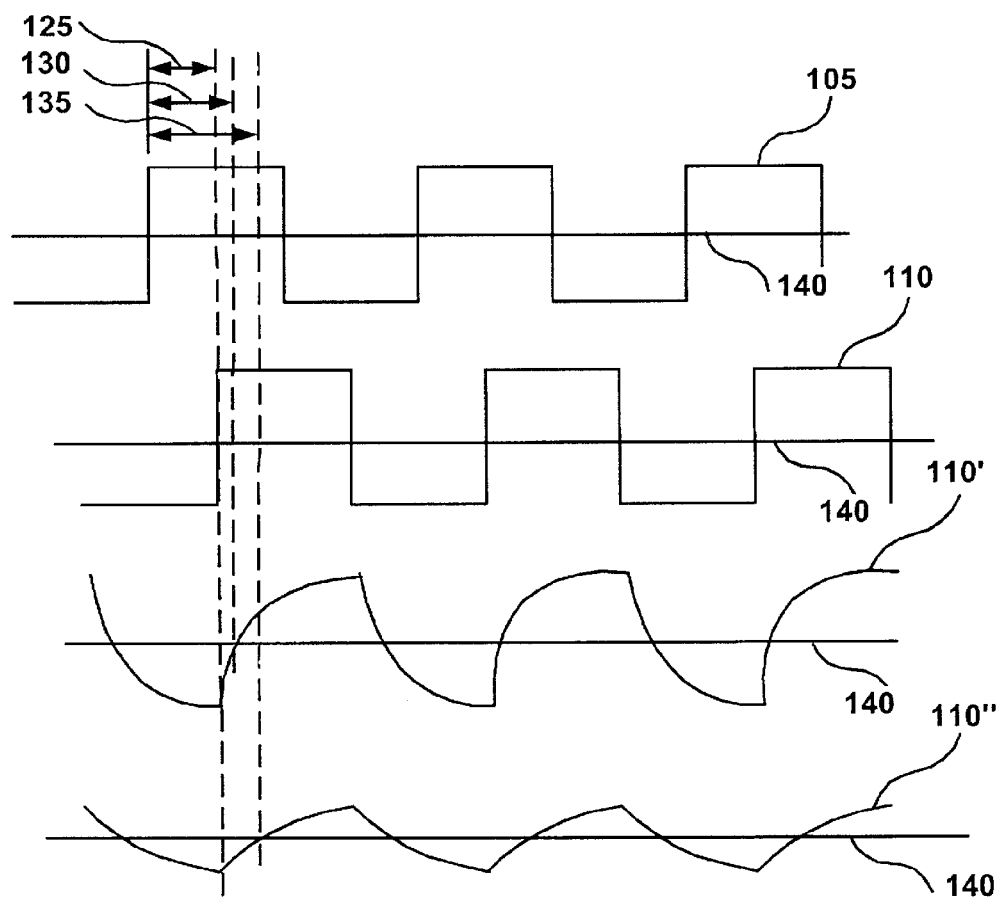
FIG. 1 is a diagram showing four time based wave forms. The first wave represents a transmitted wave. The other three waves represent received waves after the transmitted wave has been transmitted through the medium to be measured. The three waves illustrate typical received waves in an ideal medium, in a medium with moderate conductivity, and in a medium with severe conductivity respectively, the latter two illustrating degradation due to conductivity.

FIG. 1 demonstrates the propagation delay of a wave traveling through medium of similar dielectric constant but with differing conductivity. FIG. 1 is a diagram showing four time based wave forms and is useful to illustrate the problem addressed by the present invention. The first wave from the top represents a transmitted wave. The other three waves represent received waves after the transmitted wave has been transmitted through the medium to be measured. The second wave down from the top of FIG. 1 illustrates a typical received wave in an ideal medium. The third wave down from the top of FIG. 1 illustrates a typical received wave in a medium with moderate conductivity. The fourth wave down from the top of FIG. 1 illustrates a typical received wave in a medium with severe conductivity. Thus the latter two waves illustrate degradation due to conductivity.

The dielectric constant is estimated by determining the delay between the transmitted wave and the ideal received wave. Thus, if one can accurately determine the timing of the edges of the ideal received wave, one can accurately estimate the dielectric constant. However, due to limitations of inexpensive electronic used to process the received waves, the timing of the edges cannot be directly measured. First, the received waves are not ideal square waves, rather they are malformed waves, the shape being malformed by the conductivity of the target medium. Second, the detection electronics can only measured voltage levels significantly higher than the voltages at the edge crossings. Thus the detection occurs after the edge has actually occurred, and significantly the timing of the candidate voltage detection level will be affected by conductivity Specifically, the more conductive the medium, the more delay in rise time of the received wave and the later in time the detection voltage will be reached. Any delay caused by conductivity is computational error when trying to estimate the dielectric constant.

The present invention solves the problem by using hysteresis to determine multiple detection points and then deploys curve fitting mathematics to accurately interpolate and thus estimate the edge of the ideal received wave which in turn provides an accurate estimate of the dielectric constant.

Referring to FIG. 1, wave 105 depicts the transmitted wave wherein the horizontal axis is time based and the vertical axis is voltage, measured against a reference voltage line 140. Ideal received wave 110 is identical to the transmitted wave 105 except it is delayed in time. The delay interval 125 is the desired delay that provides an accurate estimate of the dielectric constant. Note that the time interval 125 intersects all three received waves at the point of inflection of each wave. The received waves 110' and 110" have been affected by conductivity and the detection edges is moved forward in time as conductivity increases. Specifically, in FIG. 1, the interval 130 illustrates the measured interval in the environment exhibiting moderate conductivity, and the interval 135 illustrates the measured interval in an environment exhibiting severe conductivity. The difference between interval 125 and interval 130 is caused by conductivity and is error that must be eliminated to accurately determine interval 125. Interval 125, once determined, can be used as an accurate estimate of the dielectric constant. Analogously, the difference between interval 125 and interval 135 is error that must be eliminated.

Figure 2:
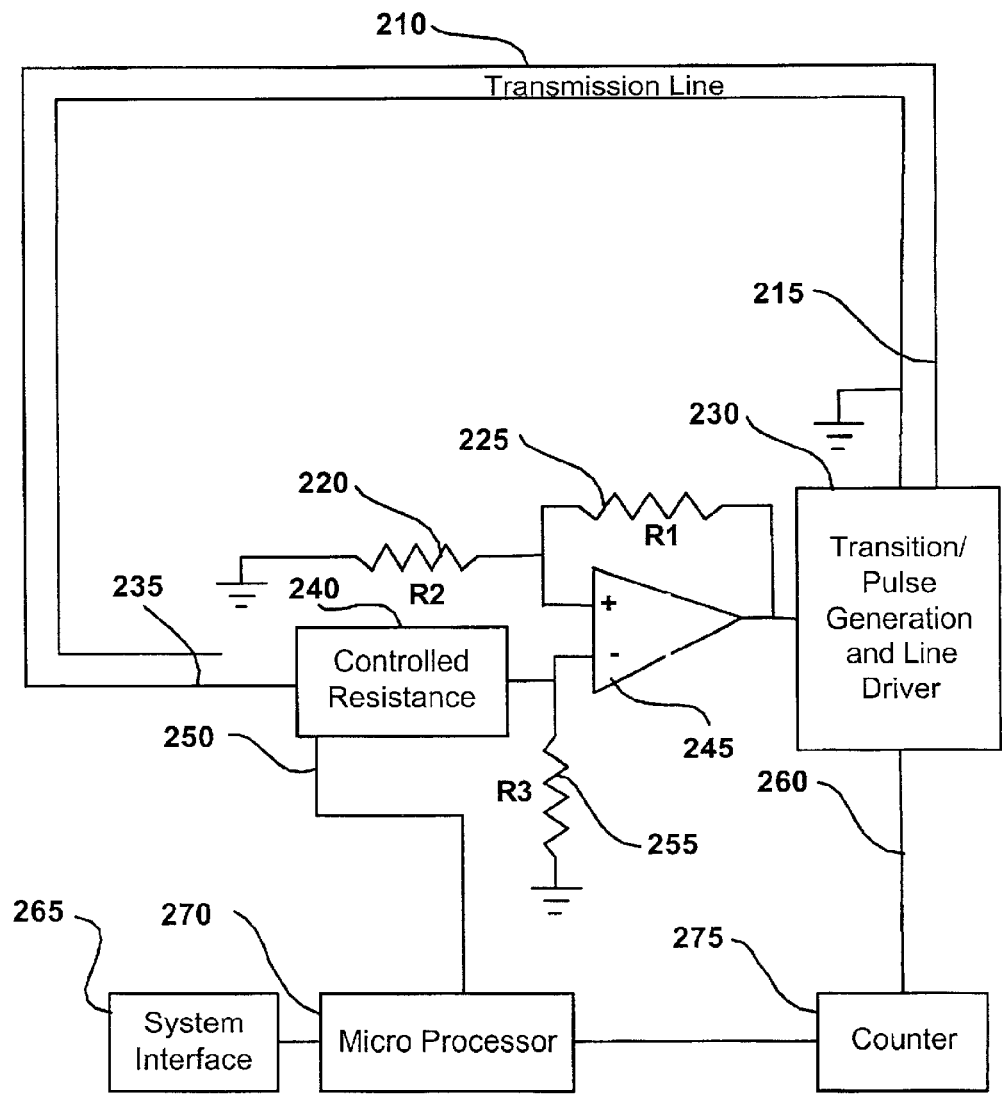
FIG. 2 is a block diagram of the preferred embodiment wherein the transmitted wave has a variable frequency and the period of the received provides a useful estimate of the dielectric constant.

FIG. 2 is a block diagram of a system implementing the correction method for processing the waves illustrated in FIG. 1. It is helpful to understand how the waves of FIG. 1 are presented to the system of FIG. 2. Referring to both FIG. 1 and FIG. 2, transmitted wave, the first wave from the top of FIG. 1, is the voltage at the sending end 215 of the transmission line 210 of FIG. 2. The ideal received wave, the second wave from the top of FIG. 1, shows the ideal wave where the transmission line 210 of FIG. 2 impedance is matched producing an exact replica of the original wave delayed in time. The received wave with moderate conductivity, the third wave from the top of FIG. 1, shows the wave as it arrives at the receiving end 235 of the transmission line 210 of FIG. 2 in a medium with moderate conductivity.

Note that there is a definite rise and fall time associated with this wave. Also note that the time it takes from the launching of the transmitted wave to the half amplitude point is definitely longer than the same half amplitude point on the ideal received wave. It is important to note that the edge of the wave sent at moderate conductivity arrives at the same time as the ideal wave, but the rise time is significantly longer. The detection method senses the center of the received wave. This extra time translates to a longer apparent time propagation time. The fourth wave from the to of FIG. 1 shows the same thing in a very conductive medium where the losses are so great as to prevent the received wave from reaching full amplitude. The point of inflection of the wave still appears at the ideal delay time, but the half amplitude point is reached significantly later. It is apparent that as conductivity increases, the apparent propagation delay increases. The intent of this invention is to offer a level of compensation to factor out the effects of rise time and therefore conductivity on the propagation delay time measurement.

Friedman (U.S. Pat. No. 3,965,416) teaches the delay line can be integrally coupled as a portion of an oscillator and produce a frequency that is a function of the dielectric constant. FIG. 1 shows the effect of conductivity on that measured frequency. The first two waves from the top of FIG. 1 show a transmitted wave and an ideal received wave. The interval 125, 130 and 135 show the components that make up the perceived propagation delay. The first interval 125 is the ideal propagation delay and the remaining intervals 130 and 135 are the portion of the delay that is induced by the pulse rise time. In the ideal trace, there is no delay that is induced by the pulse rise time. The third and fourth waves from the top of FIG. 1 show the effect of moderate and severe conductivity. Note that the delay times denoted by interval 125 are equal, but that the rise time as shown by intervals 130 and 135 increase significantly. The transmitted wave is reversed when the 50 percent threshold is crossed. Note that the transmitted wave period increases based on the amount of conductivity in the sample. The accuracy of the measurement is proportionally degraded by conductivity.

FIG. 2 illustrates the preferred embodiment that deploys the correction method. Referring again to FIG. 2, the detector apparatus is designed to have controlled hysteresis. With low hysteresis, the detection device will trigger when the received wave 235 is approximately equal to ground. In the high hysteresis case, the detection device is set such that it will not trigger until the received wave 235 of the device has not only reached ground, but has reach a predetermined threshold above ground. The actual delay can be approximated by mathematically by detecting the differences in the frequency between the two thresholds and projecting mathematically the true propagation delay. To use this technique with the detection method taught by Friedman, one would take one reading at a normal threshold and another reading at a high threshold level. The true propagation delay is then derived from the difference in the period derived from the two frequencies. The curve, though approximately linear, in not strictly linear and therefore higher order correction algorithms will yield more accurate results than the simple linear example used in this example.

FIG. 2 further illustrates a sensor apparatus composed of the following:

1. A detector comprising a high speed comparator 245, resistor 220, resistor 225, resistor 255, and controlled resistance 240.
2. Transition/Pulse Generation and Line Driver 230
3. A counter 275,
4. A transmission line 210,
5. A control section composed of a microprocessor 270, and a system interface 265.

A transition pulse generator and line driver 230 generates a pulse that is transmitted down the transmission line. When the pulse reaches the end of the delay line 235, the line begins to move to the new level at a rate determined by the rise and fall times. Control line 250 determines if the detection device is in high or low hysteresis mode. When the detection device reaches the trigger voltage level, the comparator 245 changes state causing transition/pulse generation and line driver 230 to send a new transition pulse. This next pulse travels the length of the transmission line and again triggers a high to low transition. This process will run continuously until such time as the microprocessor 270 disables it. The microprocessor will enable the counters 275 in order to count the total number of pulses. After a fixed period of time, the microprocessor 270 will stop the counter 275 and read the total number of pulses that have transversed the delay line. The microprocessor 270 will then raise the control line 250. The same process will be repeated in the other hysteresis mode. The difference in the two counter 275 readings can be used as a basis for approximating delay. The outputs are feed into the Analog to Digital converter inputs of the micro controller. The difference in voltage between the two outputs provides a correction factor to subtract from the low hysteresis channel yielding a corrected reading that is a function of the true delay of the transmission line.

Note that one detector with programmable hysteresis similar to that used in FIG. 4 and FIG. 5 can be used and reading taken sequentially. This alternative was shown to aid in explanation.

FIG. 7 gives the flow chart showing the steps in the conversion process. The moisture reading process is started with the arrival of a command request to take a reading. If a command is present, a reading at the high threshold is taken. A reading at the low threshold is then taken. The low threshold reading most accurately represents the true propagation delay, however this reading may have substantial errors due to conductivity of the media. As shown above, the processor can use the difference between the high and low threshold readings to add a degree of correction to the low threshold reading. The corrected is then provided to the processes issuing the command for the moisture reading.

Having illustrated and described the principles of this invention in a number of preferred embodiments thereof, it should be readily apparent to those skilled in the art that the invention can be modified in arrangement and detail without departing from such principles. We claim all modifications coming within the scope of the accompanying claims.

I claim:

1. A system for monitoring material having an associated dielectric constant in an environment wherein the material exhibits conductivity comprising:

an electrical signal, a transmitted waveform wherein the transmitted wave is derived from the electrical signal, a transmission line wherein the transmission line is surrounded by the material and the electrical signal is propagated through the transmission line, a received waveform wherein the received waveform is derived from the electrical signal after the electrical signal has propagated through the transmission line, the received waveform further includes a propagation delay component and a pulse rise-time component, the propagation delay component reflects the propagation time between the transmitted waveform and the received waveform, a decoder for decoding the received waveform into a first component and a second component wherein the first component approximates the propagation delay component and the second component approximates the pulse rise-time component, a hysteresis adjustment wherein the second component is determined by taking a plurality of readings with varying hysteresis settings and interpolating the readings to derive the second component, wherein the first component is interpreted as an approximation of the dielectric constant of the material and is monitored.

2. The system of claim 1 wherein the electrical signal is a differential electrical signal.

3. The system of claim 2 wherein the environment is an irrigation environment and the approximation of the dielectric constant is used to monitor the moisture in the irrigation environment.

4. The system of claim 3 wherein water is applied to the environment when the approximation of the dielectric constant drops below a first threshold and water is withheld from the environment when the approximation of the dielectric constant exceeds a second threshold.

5. The system of claim 2 wherein water is applied to the environment when the approximation of the dielectric constant drops below a first threshold and water is withheld from the environment when the approximation of the dielectric constant exceeds a second threshold.

6. The system of claim 1 wherein the environment is an irrigation environment and the approximation of the dielectric constant is used to monitor the moisture in the irrigation environment.

7. The system of claim 1 wherein water is applied to the environment when the approximation of the dielectric constant drops below a first threshold and water is withheld from the environment when the approximation of the dielectric constant exceeds a second threshold.

8. A method for monitoring material having an associated dielectric constant in an environment wherein the material exhibits conductivity comprising the steps of:

associating an electrical signal with the environment, associating a transmitted waveform with the electrical signal wherein the transmitted wave is derived from the electrical signal, associating a transmission line with the environment wherein the transmission line is surrounded by the material and the electrical signal is propagated through the transmission line, associating a received waveform with the electrical signal wherein the received waveform is derived from the electrical signal after the electrical signal has propagated through the transmission line, the received waveform further includes a propagation delay component and a pulse rise-time component, the propagation delay component reflects the propagation time between the transmitted waveform and the received waveform, associating a decoder for decoding the received waveform into a first component and a second component with the environment wherein the first component approximates the propagation delay component and the second component approximates the pulse rise-time component, associating a hysteresis adjustment with the hysteresis adjustment wherein the second component is determined by taking a plurality of readings with varying hysteresis settings and interpolating the readings to derive the second component, wherein the first component is interpreted as an approximation of the dielectric constant of the material ad is monitored.

9. The method of claim 8 wherein the electrical signal is a differential electrical signal.

10. The method of claim 9 wherein the environment is an irrigation environment and the approximation of the dielectric constant is used to monitor the moisture in the irrigation environment.

11. The method of claim 10 wherein water is applied to the environment when the approximation of the dielectric constant drops below a first threshold and water is withheld from the environment when the approximation of the dielectric constant exceeds a second threshold.

12. The method of claim 9 wherein water is applied to the environment when the approximation of the dielectric constant drops below a first threshold and water is withheld from the environment when the approximation of the dielectric constant exceeds a second threshold.

13. The method of claim 8 wherein the environment is an irrigation environment and the approximation of the dielectric constant is used to monitor the moisture in the irrigation environment.

14. The method of claim 8 wherein water is applied to the environment when the approximation of the dielectric constant drops below a first threshold and water is withheld from the environment when the approximation of the dielectric constant exceeds a second threshold.

* * * * *